United States Patent [19]
Moesle, Jr.

[11] Patent Number: 5,417,204
[45] Date of Patent: May 23, 1995

[54] SCUBA AIR CONTAMINATION DETECTOR

[75] Inventor: James W. Moesle, Jr., Naples, Fla.

[73] Assignee: Robert H. Kessler, Weston, Conn.; a part interest

[21] Appl. No.: 115,932

[22] Filed: Sep. 1, 1993

[51] Int. Cl.$^6$ .......................... A62B 7/00; A62B 9/00; A61M 16/00; G08B 3/00

[52] U.S. Cl. .......................... 128/205.23; 128/204.18; 128/202.22; 128/202.14; 73/863.71; 73/23.2; 73/31.03; 422/86

[58] Field of Search ....................... 128/202.22, 202.27, 128/200.24, 204.18, 205.22, 205.23, 202.14; 422/86, 87; 73/864.33, 863.71, 23.2, 23.34, 31.03

[56] References Cited

U.S. PATENT DOCUMENTS

| | | | |
|---|---|---|---|
| 1,146,531 | 7/1915 | Smyly | 422/86 |
| 1,537,519 | 5/1925 | Yablick | 422/119 |
| 3,570,808 | 3/1971 | Wrenn | 128/202.27 |
| 3,585,963 | 6/1971 | Hiszpanski | 116/117 |
| 4,014,216 | 3/1977 | Thornton et al. | 73/863.23 |
| 4,154,586 | 5/1979 | Jones et al. | 55/274 BN |
| 4,154,794 | 5/1979 | Clyne | 422/86 |
| 4,256,694 | 3/1981 | McAllister et al. | 422/58 |
| 4,365,627 | 12/1982 | Wing | 128/202.22 |
| 4,449,524 | 5/1984 | Gray | 128/202.27 |
| 4,461,184 | 7/1984 | Gandhi et al. | 73/863.23 |
| 4,656,008 | 4/1987 | Gump | 422/86 |
| 4,728,499 | 3/1988 | Fehder | 422/56 |
| 4,994,117 | 2/1991 | Fehder | 436/133 |
| 5,116,088 | 5/1992 | Bird | 285/319 |

OTHER PUBLICATIONS

"Scuba Accessories", *Skin Diver Magazine*, Dec. 1993, pp. 22-23.

*Primary Examiner*—Kimberly L. Asher
*Attorney, Agent, or Firm*—David N. Koffsky

[57] ABSTRACT

An air contamination detector for a scuba unit includes a transparent tube having a lumen, the lumen being user visible for a full 360° about its circumference. A contamination indicator is positioned within the lumen and is exposed to air flow from the air supply of the scuba unit. The contamination indicator is responsive to a contaminant to manifest a change that is visible through the transparent tube. A quick connect/disconnect air connection is affixed to one end of the transparent tube and mates with a low pressure fitting that communicates with the scuba air tanks. A further quick connect/disconnect air filling is positioned at another end of the transparent tube and is connectable to a hose that provides air inlet control for a buoyancy control vest. Since the air inlet control includes a user-operable air inlet valve, air quality within the air tanks can be tested simply by depressing the buoyancy control air inlet valve to enable air to pass through the transparent tube and over the contamination detector.

7 Claims, 1 Drawing Sheet

SCUBA AIR CONTAMINATION DETECTOR

FIELD OF THE INVENTION

This invention relates to self-contained underwater breathing apparatus (scuba) and, more particularly, to a detector for indicating when contaminated air is present in such scuba apparatus.

BACKGROUND OF THE INVENTION

Scuba divers often need to rely on unknown quality air sources when having their high pressure tanks filled with air. If the compressor employed to fill a scuba tank is not properly set up, operated and maintained, contaminants may be introduced into air fed to the scuba tank. For instance, if the compressor's air intake is positioned too close to the exhaust outlet, carbon monoxide may be introduced into the air flow and thus into the air tanks. Further, if the compressor is not well maintained, both carbon monoxide and/or oil vapors may be introduced into the air through internal engine pathways.

While some air contaminants will taste and smell foul, other contaminants can be odorless and tasteless, e.g. carbon monoxide. Prior to diving, most careful divers will test the air in a dive tank to determine if it exhibits any unusual taste or smell. If such an off-taste or smell is detected, the cautious diver will not use the tank. Unfortunately, there is no way carbon monoxide can be detected by such an empirical test.

The prior art evidences a number of self-contained gas detection units for insertion into gas flow conduits. U.S. Pat. No. 4,728,499 to Fehder describes a device for the detection of carbon dioxide in a concentration of more than 2% in a gas flow. Fehder employs a hygroscopic high boiling, transparent, water miscible liquid and a pH sensitive indicator. Changes in the pH indicator can be determined by a user viewing the detector through a small window. U.S. Pat. No. 3,585,963 to Hiszpanski discloses a similar structure for inclusion in a fluid flow system wherein a moisture indicator, by Change of color, can be viewed through a small viewing window. U.S. Pat. Nos. 1,537,519 to Yablick and 4,365,627 to Wing both describe gas flow canisters wherein a state of contamination of a filter element is detectable through a viewing window or aperture. A similar structure is shown in U.S. Pat. No. 1,146,531 wherein a paper gas detector is positioned near a viewing window within a gas passage canister. When the indicator paper changes color, such change can be detected by the user by viewing the paper.

While all of the above prior art describes various fluid contamination detectors, none are designed for application to a scuba unit. For instance, scuba units employ multiple hose connections that are of the quick connect/disconnect variety. Those connectors are gas tight and assure female/male and or male/female air tight connections. However, they do not assure any particular relative angular orientation as between the units being connected. Thus, the provision of a window or limited viewing aperture, as suggested by the prior art, for viewing a contamination detector, can not be safely used in a scuba apparatus as the window portion may be aligned so as to be pointed away from the user's direction of vision. Furthermore, during use, such a windowed detector may become rotated. It is vital in scuba applications that safety equipment be always clearly visible to the user and, in no way, obscured.

Accordingly, it is an object of this invention to provide a gas contamination detector specifically designed for use in scuba apparatus.

It is another object of this invention to provide a gas detector for scuba apparatus wherein quick connect/disconnect connectors are employed.

It is yet another object of this invention to provide a gas contamination detector for scuba apparatus wherein the contamination detector is always viewable by the diver.

It is a still further object of this invention to provide a gas contamination detector for scuba apparatus which requires no modification to the scuba apparatus.

SUMMARY OF THE INVENTION

An air contamination detector for a scuba unit includes a transparent tube having a lumen, the lumen being user visible for a full 360° about its circumference. A contamination indicator is positioned within the lumen and is exposed to air flow from the air supply of the scuba unit. The contamination indicator is responsive to a contaminant to manifest a change that is visible through the transparent tube. A quick connect/disconnect air connection is affixed to one end of the transparent tube and mates with a low pressure fitting that communicates with the scuba air tanks. A further quick connect/disconnect air filling is positioned at another end of the transparent tube and is connectable to a hose that provides air inlet control for a buoyancy control device. Since the air inlet control includes a user-operable air inlet valve, air quality within the air tanks can be tested simply by depressing the buoyancy control air inlet valve to enable air to pass through the transparent tube and over the contamination detector.

DETAILED, DESCRIPTION OF THE INVENTION

Figure 1:
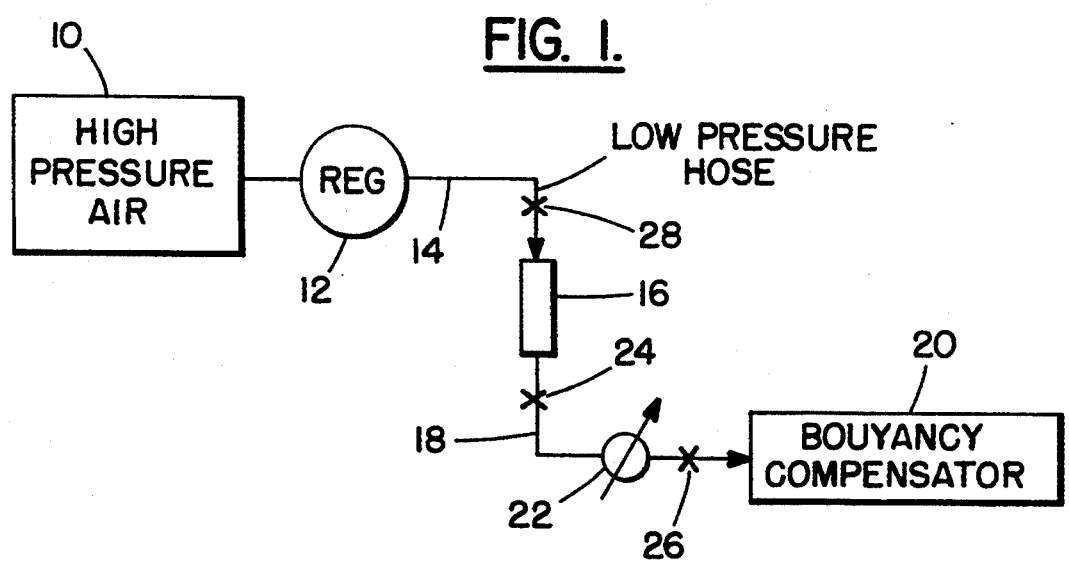
FIG. 1 is a block diagram illustrating the major components of a scuba unit, including an air contamination detector constructed in accordance with the invention.

Referring to FIG. 1, a scuba apparatus is illustrated that includes a high pressure air supply 10 which feeds air via a regulator 12 to a low pressure air hose 14. The remaining outputs from regulator 12 that are employed for the diver's breathing apparatus are not shown to avoid over complication of the view. Low pressure air hose 14 feeds an air contamination detector 16 whose construction will be detailed below with respect to FIGS. 2-4.

Air passing through low pressure hose 14 proceeds through air contamination detector 16 and into an air inlet hose 18 for a buoyancy compensator 20. A user actuatable valve 22 is positioned within hose 18 and enables air to be introduced into buoyancy compensator 20, selectively. Hose 18 includes quick connect/disconnect air fittings 24 and 26 at its ends. Low pressure hose 14 includes a screw fitting at regulator 12 and a quick connect/disconnect fitting 28 which, ordinarily, would mate with connect/disconnect fitting 24. Air contamination detector 16 is designed to fit between low pressure hose 14 and hose 18 and to mate directly with the connect/disconnect fittings 24 and 28.

Figure 2:
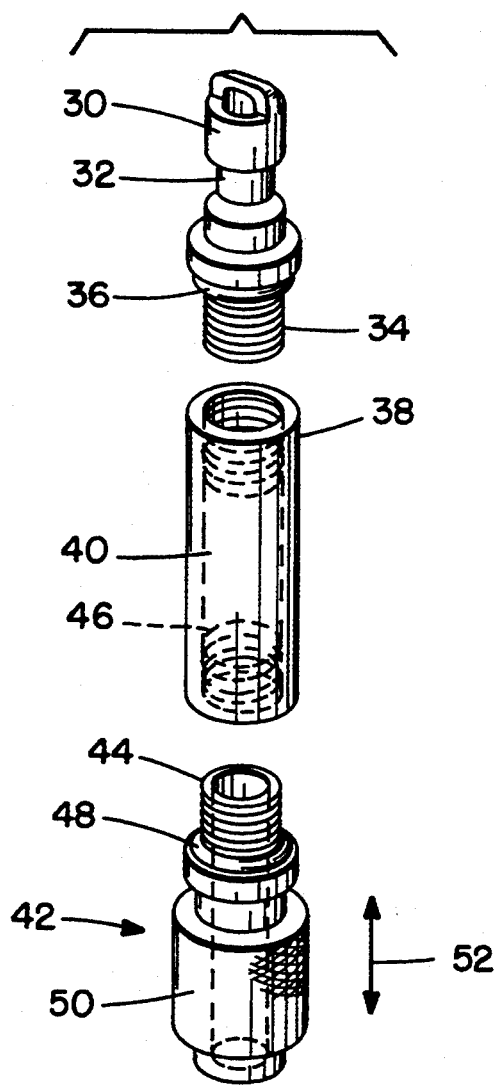
FIG. 2 is an exploded view of an air contamination detector of the invention.
Figure 3:
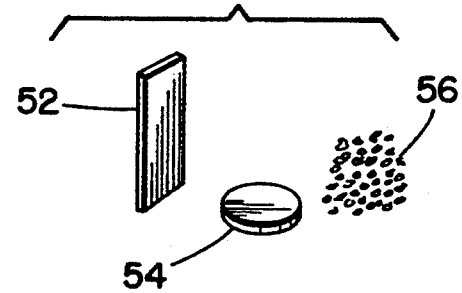
FIG. 3 illustrates a variety of contamination detectors which can be emplaced within the air contamination detector of FIG. 2.

In FIG. 2, an exploded view is shown of a preferred embodiment of the air contamination detector 16. A male connect/disconnect fitting 30 of known type includes an indented region 32 that is engaged by detents within a mating female connect/disconnect fitting (not shown). A lower-most portion 34 of male fitting 30 is threaded and includes an o ring 36 positioned thereabout. Threaded portion 34 is received by internal threads within a hollow, transparent, plastic cylinder 38. Cylinder 38 includes a lumen 40 that is continuous throughout its entire length and is fully transparent about its entire 360° periphery. Lumen 40 is designed to accommodate a contamination detector that exhibits a physical change in response to the presence of a contaminant in air flowing through lumen 40. In substantially all instances, a contaminant detector must be able to detect the presence of carbon monoxide in the air flow.

The lower-most portion of transparent cylinder 38 mates with a female quick connect/disconnect fitting 42 that includes a threaded portion 44 that mates with internal threads 46 within lumen 40. An o ring 48 enables an air tight seal to be achieved when fitting 42 is mounted and screwed into threaded area 46. A slidably mounted sleeve 50 controls the internal workings of detents present within fitting 42. Sleeve 50 is spring biased and is movable in the directions shown by arrows 51 so as to enable interconnection with a further male quick connect/disconnect fitting such as is shown at 30 in FIG. 2.

Cylinder 38 is preferably comprised of a high strength, clear, polymeric material having a wall thickness that can withstand both internal air pressures that occur on low pressure air hose 14 (e.g.=135 psi) and external dive pressures that are experienced by a diver. A preferred material for cylinder 38 is a polycarbonate or other high, similar, non-flexible, polymeric material. The walls of cylinder 38 must be highly transparent so as to enable a user to clearly view the state of an air contamination detector positioned within lumen 40. The preferred dimensions are 1¾" in length; ⅜" in diameter with lumen 40 exhibiting a ¼" inner diameter. Transparency can be assured by either injection moulding cylinder 38 or by vapor polishing of the surface of polycarbonate cylinder 38 with methylene chloride if lumen 40 is drilled.

As above indicated, an air contamination detector is positioned within lumen 40. It is preferred that the air contamination detector be capable of manifesting the presence of low levels of carbon monoxide in air flow through lumen 40. For instance, a strip of paper 52 that has been impregnated with palladium chloride will provide an indication of the presence of carbon monoxide. The palladium chloride, in the presence of carbon monoxide, manifests a black metallic palladium which is clearly visible through the transparent walls of cylinder 38. Carbon monoxide detectors also come in button size such as shown at 54, and in pellet size such as shown at 56. Carbon monoxide detector buttons may be obtained from American Gas Chemical Company, Ltd., 220 Pegasus Avenue, North Vale, N.J. 07647. Such buttons manifest a color change in quantities of carbon monoxide as low as 50 parts per million (over a 7–8 minute period). As carbon monoxide concentration is increased, a distinct color change can be evidenced in as little as one minute. Similar color changes take place when a carbon monoxide pellet detector material 56 is used.

While the most important contaminant to be detected in an air supply is carbon monoxide, it is also useful to detect the presence of petroleum hydrocarbon vapors. A paper substrate is first coated with a silica gel and then treated with chromic acid and can also be inserted into lumen 44 for oil vapor detection. The chromic acid will change from orange to greenish brown in the presence of petroleum hydrocarbon vapors. (Such strips may be obtained from National Drager, P.O. Box 120, Pittsburgh, Pa. 15230.)

Figure 4:
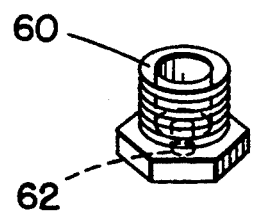
FIG. 4 illustrates an alternative closure means for one end of the air contamination detector of FIG. 2.

If it is not desired to connect the air contamination detector to a buoyancy compensator, the termination fitting shown at 60 in FIG. 4 can be used. FIG. 4 illustrates an end seal that has an air passage aperture 62 which communicates with lumen 40. Thus, by simply connecting male fitting 30 to low pressure hose 14 (when fitting 60 is present) and allowing air to pass through the air contamination detector, contaminants can be sensed.

As can be seen from the above, an air contamination detector for a scuba unit has been described which is readily insertable into already existing quick connect-/disconnect scuba fittings; allows viewing of the contamination detector about its entire circumference and is usable both during a dive and prior to a dive to determine air tank quality.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. Apparatus including a contamination detector in combination with a scuba unit that includes a high pressure air supply, said apparatus comprising:

a transparent tube with a lumen, said lumen being user-visible for a full 360° about a circumference of said transparent tube; a contamination indicator positioned within said lumen and exposed to air flow from said high pressure air supply through said lumen, said contamination indicator responsive to at least a carbon monoxide contaminant in said air flow to manifest a change that is visible to a user through said transparent tube;

a first quick connect/disconnect fitting affixed to one end of said transparent tube, and mating with a low pressure fitting in said scuba unit, said low pressure fitting communicating with said air supply; and fitting means at a second end of said transparent tube, said fitting means maintaining said contamination indicator within said lumen and having an orifice that enables passage of air from said lumen, at least one of said first quick connect/disconnect means or said fitting means removable from said transparent tube to enable replacement of said contamination indicator.

2. The apparatus as recited in claim 1, wherein said transparent tube is threaded at both ends for receiving said quick connect/disconnect fitting and said fitting means.

3. The apparatus as recited in claim 2 wherein said fitting means is a second quick connect/disconnect fitting that is threadedly engaged with said transparent tube, said second quick connect/disconnect fitting releaseably connecting to an air connector leading to a buoyancy compensator, said air connector including a valve, responsive to user actuation, that creates an air passage through said contamination detector and into said buoyancy compensator.

4. The apparatus as recited in claim 3, wherein said transparent tube is comprised of a hollow, clear, polymeric cylinder having a wall thickness sufficient to withstand externally applied dive pressures and an internal flow of pressurized air from a low pressure supply emanating from said scuba unit.

5. The apparatus as recited in claim 4, wherein said contamination indicator comprises a chemically treated carrier which indicates, by change of color, a presence of carbon monoxide.

6. The apparatus as recited in claim 4, wherein said contamination indicator further comprises a chemically treated carrier which manifests a color change upon an appearance of oil vapors in air flow through said lumen.

7. The apparatus as recited in claim 1, wherein said first quick connect/disconnect fitting is a male quick release connector and said fitting means is a female quick connect/disconnect fitting.

* * * * *